United States Patent [19]

Kleemann et al.

[11] 4,398,042
[45] Aug. 9, 1983

[54] PROCESS FOR THE PRODUCTION OF 3-MERCAPTO-PROPANEDIOL-(1,2)

[75] Inventors: Axel Kleemann; Robert Nygren; Rüdolf Wagner, all of Hanau, Fed. Rep. of Germany

[73] Assignee: Degussa Aktienbesellschaft, Frankfurt, Fed. Rep. of Germany

[21] Appl. No.: 252,608

[22] Filed: Apr. 9, 1981

[30] Foreign Application Priority Data

Apr. 12, 1980 [DE] Fed. Rep. of Germany ....... 3014165

[51] Int. Cl.$^3$ .......................................... C07C 148/00
[52] U.S. Cl. ..................................................... 568/62
[58] Field of Search ........................................... 568/62

[56] References Cited

U.S. PATENT DOCUMENTS 3,462,496  8/1969  Fletcher et al. ...................... 568/62
3,574,768  4/1971  Tompkins ............................. 568/62
4,281,202  7/1981  Buchholz et al. ..................... 568/62

FOREIGN PATENT DOCUMENTS 910296  4/1954  Fed. Rep. of Germany .

OTHER PUBLICATIONS

Smith, Berichte Deutsch. Chem. Ges. vol. 69, pp. 678–680, (1936).
Sjoberg, Berichte Deutch. Chem. Ges. vol. 75, pp. 13–29, (1942).

Primary Examiner—Bernard Helfin
Attorney, Agent, or Firm—Cushman, Darby & Cushman

[57] ABSTRACT

The production of 3-mercapto-propanediol-1,2 is attained with good yields and in an industrially simple manner by reacting liquid hydrogen sulfide with glycidol under pressure, namely either in the presence of aluminum oxide or a sodium aluminum silicate, i.e., in heterogeneous phase or in the presence of an alkali or alkaline earth hydroxide dissolving in reaction medium, i.e. in homogeneous phase.

24 Claims, No Drawings

PROCESS FOR THE PRODUCTION OF 3-MERCAPTO-PROPANEDIOL-(1,2)

BACKGROUND OF THE INVENTION

In the literature until today there are described in the literature two processes according to which 3-mercapto-propanediol-1,2, also called monothioglycerine, can be produced by the addition of hydrogen sulfide to glycidol.

According to L. Smith and B. Sjöberg (Ber. deutsch. chem. Ges. Vol. 69, pages 678–680, (1936)) and Sjöberg (Ber. deutsch. chem. Ges. Vol. 75, pages 13–29, (1942)) $\frac{1}{3}$ mole of glycidol is dropped into a solution of $\frac{1}{3}$ mole barium hydrogen sulfide saturated with hydrogen sulfide with running introduction of hydrogen sulfide. In the highest case the yield according to this process is 61% of theory, whereby it is stated that in increasing the charge beyond $\frac{1}{3}$ mole the yield drops off. Besides there are formed higher molecular weight condensation products of glycidol. By distillation monothioglycerine can be separated from water and the byproducts. Because of the difficulties in enlarging the charge this method of production does not represent an industrially usable process for making monothioglycerine.

In German Pat. No. 910296 there is described a continuous process for the production of monothioglycerine whereby there should be produced yields of about 80–95%. Hereby there is employed a recycling apparatus which is charged with aqueous alcohol, e.g. isopropanol, and catalytic amounts, e.g. 0.3% of alkali or alkaline earth hydrogen sulfide, such as calcium hydrogen sulfide. Gaseous hydrogen sulfide is introduced into the apparatus in such manner that continuously hydrogen sulfide is present in the form of finely divided gas bubbles in the entire apparatus or solution and its concentration is greatest at the place of introduction of the glycidol. The temperature of the reaction mixture is held between 20° and 35° C. The reaction mixture is continuously drawn off from the recirculating apparatus.

By introduction of carbon dioxide the catalyst is precipitated as carbonate, the solution subsequently filtered and the alcohol employed recovered by distillation. The water is removed in a next distillation step and the residue finally subjected to fractionation in vacuum whereby then monothioglycerine is obtained. In all of the examples the catalyst is removed before the distillation of the product from the crude product in order that the distillation of the product should proceed without difficulties.

In the first place the known process is tied to a special apparatus since there must be continuously present sufficient hydrogen sulfide to catch the hydroxide formed from the hydrogen sulfide. Otherwise, condensation reactions occur between glycidol and the monothioglycerine formed.

Besides the catalyst employed after the end of the reaction must be converted into a carbonate by introduction of carbon dioxide. The carbonate cannot be inserted again as such.

Furthermore, the distillation of the crude product can not be carried out in the presence the catalyst carbonate.

Therefore, the object of the invention is the development of a process which is industrially simple to carry out which likewise leads to high yields.

SUMMARY OF THE INVENTION

It has now been found that monothioglycerine can be produced in high yields in an industrially simple manner if liquid hydrogen sulfide is allowed to react with glycidol in the presence of a catalyst in heterogeneous or homogeneous phase.

As solid catalysts which do not dissolve in the reaction medium there are particularly well suited weakly basic catalysts such as aluminum oxide, preferably activated alumina containing 0.02 to 5 weight % alkali, sodium aluminum silicates such as zeolites and hydroxysodalite. These solid catalysts are distinguished by a high time on stream. They are preferably employed as solid bed catalysts. A very suitable zeolite is e.g., montmorillonite. As catalysts for working in homogeneous phase there are suited alkali and alkaline earth metal hydroxides which are soluble in the reaction medium of glycidol and liquid hydrogen sulfide, e.g. sodium hydroxide potassium hydroxide, calcium hydroxide, and barium hydroxide. Sodium hydroxide and potassium hydroxide are preferred.

The process is carried out under pressures of 15 to 200 bar.

The temperature in the heterogeneous phase at the solid bed is between 30° and 150° C., in the homogeneous phase generally at the upper mentioned temperature limit or somewhat higher. Generally temperatures of 30° to 180° C. are employed.

The molar ratio of liquid hydrogen sulfide to glycidol is between 3:1 to 10:1, preferably 4:1 to 6:1, independent of whether operating in heterogeneous or homogeneous phase.

The process can be carried out either continuously or discontinuously (batchwise).

For example, a continuous carrying out of the process with solid bed catalyst will be explained in more detail.

Liquid hydrogen sulfide and glycidol were dosed into a solid bed reactor filled with catalyst via two pumps.

The pressure which is necessary in order to keep hydrogen sulfide in the liquid phase is controlled through a pressure release valve at the outlet of the solid bed reactor.

The desired temperature in the solid bed reactor was maintained by withdrawal of heat of reaction via the outer jacket.

The reaction mixture was relieved to atmospheric pressure via the pressure release valve. Hereby the excess hydrogen sulfide escaped nearly quantitatively. After condensation it can be returned again to the reaction system.

The reaction product remaining behind which is free of catalyst and only contains still about 0.25 weight % of hydrogen sulfide is subsequently purified by distillation under a vacuum.

It has been found that a molar ratio of "hydrogen sulfide:glycidol" below 3:1 the yield of monothioglycerine is greatly reduced and in the same measure the formation of the bis adduct of glycidol to hydrogen sulfide (bis-(2,3-dihydroxy-propyl)sulfide increases. The molar ratio "hydrogen sulfide:glycidol" in itself does not set an upper limit. However, it does show that from a molar ratio of 6:1 a substantial increase in yield no longer occurs but probably a reduction of the space-time yield.

The temperature range at which the reaction is carried out should be chosen below 150° C. when working in the heterogeneous phase since over this temperature in heterogeneous phase appreciable self condensation of glycidol leads to increasingly larger losses of yield. The reaction temperature, however, should not be chosen below 30° C. in order that the addition proceeds with economically meaningful speed. Between 30° and 150° C. there could not be established any temperature influence on the yield of monothioglycerine in heterogeneous phase.

In homogeneous phase it is also possible to exceed 150° C. and still obtain a yield of about 81% of theory, see Example 10.

As stated in carrying out the reaction there is no need to be limited to the above-described continuous method of working. The addition likewise permits carrying out the process in autoclaves or other pressure reactors discontinuously.

With homogeneous catalysis likewise yields of up to 95% of theory can be obtained, see Example 8. At a temperature above 150° C., however, the yield obtained is reduced but as already stated, still a value of around 81%.

With homogeneous catalysis there is obtained a crude product which contains the catalyst in dissolved form. Surprisingly the presence of the catalyst in the crude product does not create a problem in the distillative working up and therefore does not lead to loss in yield. The use of the homogeneous catalysis is especially suited for disontinuous operation in autoclaves or stirred containers.

Finally it is also possible to carry out the reaction between liquid hydrogen sulfide and glycidol in the presence of small amounts of solvents such as water or lower aliphatic alcohols, e.g. alkanols such as methanol, ethanol, propanol-1 and propanol-2. Glycidol and solvent are used in the weight ratio 1:0.5 to 1:5.

Monothioglycerine is an industrially interesting synthesis building block and can be employed:

in hair cosmetics, see U.S. Pat. No. 3,415,606;
in depilatory agents, see German OS 2253117;
as protective agent against UV and X-rays, see Protoplasma Vol. 45, page 293;
for the stabilization of medicinal preparations, see U.S. Pat. No. 3,026,248;
in photographic developer solutions, see French Pat. No. 1410426;
as color stabilizer in polymers, see Webb U.S. Pat. No. 2,560,053;
as enzyme activator in enzyme containing wshing agents, see German OS 1953816.

Unless other indicated, all parts and percentages are by weight.

The process can comprise, consist essentially of, or consist of the steps set forth with the stated materials.

The invention will be explained in more detail in connection with the following examples:

DETAILED DESCRIPTION

Example 1

A 2 liter stainless steel autoclave was charged with 10 grams of aluminum oxide (spherical, diameter 2–4 mm, BET surface area=300 m$^2$/g, Na$_2$O=0.08 weight %). 1020 Grams of liquid hydrogen sulfide (30 moles) and 444 grams of glycidol (6 moles) were charged. The mixture was heated with stirring for 4 hours at 70° C.

Subsequently the autoclave was relieved and the liquid content subjected to a vacuum distillation. At 89° C. and 0.9 mbar there were obtained 614.5 grams of 3-mercapto-propanediol-1,2-corresponding to 94.8% of theory, boiling point=95° C. (1 Torr), purity≧99.5 weight % (iodometric titration).

Example 2

A 2 liter stainless steel autoclave was charged with 50 grams of zeolite (montmorillonite), 1020 grams of liquid hydrogen sulfide (30 moles) and 444 grams of glycidol (6 moles). The mixture was heated with stirring for 4 hours at 30° C.

Subsequently the autoclave was relieved of pressure and the liquid contents subjected to a vacuum distillation. There were obtained 591 grams of 3-mercapto-propanediol-1,2, corresponding to 91.2% of theory. The boiling point and purity were the same as in Example 1.

Example 3

A 2 liter stainless steel autoclave was charged with 50 grams of hydroxysodalite, 1020 grams of liquid hydrogen sulfide (30 moles) and 444 grams of glycidol (6 moles). The mixture was treated with stirring for 4 hours at 70° C. After working up by distillation there were obtained 587 grams of 3-mercapto-propanediol-1,2, corresponding to 90.6% of theory. The boiling point and purity were the same as in Example 1.

Example 4

A 2 liter stainless steel autoclave was charged with 5 grams of aluminum oxide (spherical, diameter 4–6 mm, BET surface area 250 m$^2$/g, Na$_2$O=3 weight %), 1020 grams of liquid hydrogen sulfide and 444 grams of glycidol (6 moles). The mixture was heated with stirring for 4 hours at 70° C. After working up the crude product by distillation there were obtained 616 grams of 3-mercapto-propanediol-1,2, corresponding to 95.1% of theory.

Example 5

The experiment mentioned in Example 4 was repeated 10 times under exactly the same conditions but the same catalyst without replacement or regeneration, thus in the used condition, was always employed again. The following results were produced:

| Experiment | Yield [g] | Yield [% of theory] |
| --- | --- | --- |
| Repetition 1 | 615 | 94.9 |
| Repetition 2 | 618 | 95.3 |
| Repetition 3 | 616 | 95.0 |
| Repetition 4 | 605 | 93.3 |
| Repetition 5 | 617 | 95.2 |
| Repetition 6 | 612 | 94.5 |
| Repetition 7 | 614 | 94.7 |
| Repetition 8 | 608 | 93.8 |
| Repetition 9 | 614 | 94.7 |
| Repetition 10 | 613 | 94.6 |

After eleven uses the catalyst, namely aluminum oxide according to Example 1, thus showed no loss in its activity.

Example 6

A 2 liter stainless steel autoclave was charged with 5 grams of aluminum oxide, corresponding to Example 1, 510 grams of liquid hydrogen sulfide (15 moles) and 444 grams of glycidol (6 moles). The mixture was heated with stirring for 4 hours at 70° C. After working up by distillation there were obtained 338 grams of 3-mercapto-propanediol-1,2, corresponding to 52.2% of theory.

Example 7

A 2 liter stainless steel autoclave was charged with 5 grams of aluminum oxide, according to Example 1, 1020 grams of liquid hydrogen sulfide (30 moles) and 222 grams of glycidol (3 moles). The mixture was heated with stirring for 4 hours at 30° C. After working up by distillation there were obtained 309 grams of 3-mercaptopropanediol-1,2, corresponding to 95.3% of theory.

Example 8

A 2 liter stainless steel autoclave was charged with 1 gram of potassium hydroxide, 1020 grams of liquid hydrogen sulfide (30 moles) and 444 grams of glycidol (6 moles). The mixture was heated with stirring for 4 hours at 70° C. After working up by distillation there were obtained 612 grams of 3-mercapto-propanediol-1,2, corresponding to 94.5% of theory.

Example 9

A 2 liter stainless steel autoclave was charged with 1 gram of sodium hydroxide, 1020 grams of liquid hydrogen sulfide (30 moles) and 444 grams of glycidol (6 moles). The mixture was heated for 30 minutes at 145° C. After working up by distillation there were obtained 605 grams of 3-mercapto-propanediol-1,2, corresponding to 93.3% of theory.

Example 10

A 2 liter stainless steel autoclave was charged with 1 gram of potassium hydroxide, 1020 grams of liquid hydrogen sulfide (30 moles) and 444 grams of glycidol (6 moles). The mixture was heated for 30 minutes at 170° C. After working up by distillation there were obtained 521 grams of 3-mercaptopropanediol-1,2, corresponding to 80.5% of theory.

Example 11

There were dosed into a water jacketed container having an internal volume of 4.2 liters and filled with aluminum oxide, according to Example 1, via two pumps per hour, 444 grams of glycidol (6 moles) and 1020 grams liquid hydrogen sulfide (30 moles). The temperature inside the reactor, with the help of warm water, which was pumped through the outer jacket, was held at 50° C. The necessary pressure (35 mbar) to maintain the reaction mixture as liquid, was maintained through a pressure release regulatory valve by which the reaction mixture was relieved of pressure after passing through the reactor. The crude product obtained after running the apparatus for ten hours after working up by distillation gave 6.17 kg of monothioglycerine, corresponding to a yield of 95.2% of theory.

The reactor volume thus was so chosen that the component in deficiency, namely glycidol reacted to 100%.

In examples 4–11 also the boiling point and the purity of the product corresponded to that in Example 1.

What is claimed is:

1. In a process for the production of 3-mercaptopropanediol-1,2 by the reaction of hydrogen sulfide with glycidol in the presence of a catalyst, the improvement comprising reacting liquid hydrogen sulfide with glycidol under pressure sufficient to keep the hydrogen sulfide in liquid form and wherein the reaction is carried out in heterogeneous phase with montmorillonite or hydroxysodalite as a solid catalyst at 30°–150° C.

2. A process according to claim 1 wherein the liquid hydrogen sulfide and glycidol are employed in the molar ratio of 3:1 to 10:1.

3. A process according to claim 2 wherein the liquid hydrogen sulfide and glycidol are employed in the molar ratio of 4:1 to 6:1.

4. A process according to claim 3 wherein the reaction is carried out at a temperature of 15 to 200 bar.

5. A process according to claim 2 wherein the reaction is carried out at a pressure of 15 to 200 bar.

6. A process according to claim 1 wherein the reaction is carried out at a pressure of 15 to 200 bar.

7. A process according to claim 1 wherein the reaction is carried out in the presence of water or a low molecular weight aliphatic alcohol as a solvent.

8. A process according to claim 7 wherein the liquid hydrogen sulfide and glycidol are employed in the molar ratio of 3:1 to 10:1.

9. A process according to claim 8 wherein the solvent is an alkanol having 1 to 3 carbon atoms.

10. A process according to claim 1 carried out batchwise and wherein the same catalyst is employed for successive batches of liquid hydrogen sulfide and glycidol.

11. A process according to claim 10 wherein the same catalyst is employed for at least 11 batches.

12. A process according to claim 1 wherein the catalyst is montmorillonite.

13. A process according to claim 12 wherein the liquid hydrogen sulfide and glycidol are employed in the molar ratio of 4:1 to 6:1.

14. A process according to claim 12 wherein the liquid hydrogen sulfide and glycidol are employed in the molar ratio of 3:1 to 10:1.

15. A process according to claim 14 wherein the liquid hydrogen sulfide and glycidol are employed in the molar ratio of 3:1.

16. A process according to claim 12 wherein the same catalyst is employed for successive batches of liquid hydrogen sulfide and glycidol.

17. A process according to claim 16 wherein the same catalyst is employed for at least 11 batches.

18. A process according to claim 1 wherein the catalyst is hydroxysodalite.

19. A process according to claim 18 wherein the liquid hydrogen sulfide and glycidol are employed in the molar ratio of 4:1 to 6:1.

20. A process according to claim 18 wherein the liquid hydrogen sulfide and glycidol are employed in the molar ratio of 3:1 to 10:1.

21. A process according to claim 19 wherein the liquid hydrogen sulfide and glycidol are employed in the molar ratio of 3:1.

22. A process according to claim 18 wherein the same catalyst is employed for successive batches of liquid hydrogen sulfide and glycidol.

23. A process according to claim 22 wherein the same catalyst is employed for at least 11 batches.

24. A process according to claim 1 wherein the liquid hydrogen sulfide and glycidol are employed in the molar ratio of 5:1.

* * * * *